United States Patent
Johansen

[11] Patent Number: 5,820,578
[45] Date of Patent: Oct. 13, 1998

[54] BANDAGE

[76] Inventor: Christen Johansen, c/o Loeffler Johansen Bennett 821 Broadway, New York, N.Y. 10003

[21] Appl. No.: 598,831

[22] Filed: Feb. 5, 1996

[51] Int. Cl.⁶ .................................................. A61F 13/00
[52] U.S. Cl. .............................. 602/57; 602/41; 602/54; 602/56
[58] Field of Search ................ 602/41–59; 128/888, 128/889, 890; 604/174, 180; D24/189, 190, 191, 192

[56] References Cited

U.S. PATENT DOCUMENTS

| | | |
|---|---|---|
| Re. 31,886 | 5/1985 | Hodgson .................................. 428/40 |
| Re. 31,887 | 5/1985 | Hodgson ................................. 428/355 |
| 2,823,672 | 2/1958 | Schladermundt et al. ............... 602/57 |
| 3,464,408 | 9/1969 | Hamlin . |
| 3,521,631 | 7/1970 | Gardner et al. .......................... 602/42 |
| 3,529,597 | 9/1970 | Fuzak . |
| 3,645,835 | 2/1972 | Hodgson . |
| 3,687,136 | 8/1972 | Carmody . |
| 3,880,159 | 4/1975 | Diamond . |
| 4,285,338 | 8/1981 | Lemelson . |
| 4,333,449 | 6/1982 | Müller et al. . |
| 4,513,739 | 4/1985 | Johns . |
| 4,526,166 | 7/1985 | Silber . |
| 4,614,183 | 9/1986 | McCracken et al. . |
| 4,661,099 | 4/1987 | von Bittera et al. ................... 604/290 |
| 4,664,106 | 5/1987 | Snedeker . |
| 4,706,662 | 11/1987 | Thompson . |
| 4,744,355 | 5/1988 | Faasse, Jr. . |
| 4,753,232 | 6/1988 | Ward . |
| 4,780,168 | 10/1988 | Beisang et al. . |
| 4,807,613 | 2/1989 | Koehnke et al. . |
| 4,815,457 | 3/1989 | Mazars et al. . |
| 4,832,008 | 5/1989 | Gilman . |
| 4,832,009 | 5/1989 | Dillon . |
| 4,837,062 | 6/1989 | Dunshee et al. ......................... 428/41 |
| 4,858,604 | 8/1989 | Konishi . |
| 4,890,608 | 1/1990 | Steer . |
| 4,901,714 | 2/1990 | Jensen . |
| 4,907,579 | 3/1990 | Kum . |
| 4,913,138 | 4/1990 | Yoshida et al. . |
| 4,917,112 | 4/1990 | Kalt . |
| 4,935,087 | 6/1990 | Gilman . |
| 5,000,172 | 3/1991 | Ward ........................................ 602/57 |
| 5,098,500 | 3/1992 | Reed et al. . |
| 5,099,832 | 3/1992 | Ward ........................................ 602/57 |
| 5,147,698 | 9/1992 | Cole ......................................... 428/40 |
| 5,153,040 | 10/1992 | Faasse, Jr. ............................... 428/40 |
| 5,183,459 | 2/1993 | Bernard ................................... 602/52 |
| 5,213,565 | 5/1993 | Rollband ................................. 602/41 |
| 5,230,701 | 7/1993 | Meyer et al. ............................ 602/76 |
| 5,244,457 | 9/1993 | Karami et al. .......................... 602/55 |
| 5,264,218 | 11/1993 | Rogozinski ............................ 424/445 |
| 5,266,371 | 11/1993 | Sugii et al. ............................. 428/40 |
| 5,275,284 | 1/1994 | Onotsky ................................. 206/441 |
| 5,308,313 | 5/1994 | Karami et al. .......................... 602/55 |
| 5,328,449 | 7/1994 | Andrews et al. ........................ 602/42 |
| 5,328,450 | 7/1994 | Smith et al. ............................. 602/59 |
| 5,333,753 | 8/1994 | Etherdge ................................. 221/33 |
| 5,336,162 | 8/1994 | Ota et al. ................................. 602/41 |
| 5,376,067 | 12/1994 | Daneshvar ............................... 602/58 |

*Primary Examiner*—Richard J. Apley
*Assistant Examiner*—Kim M. Lee
*Attorney, Agent, or Firm*—Donald S. Dowden; Cooper & Dunham LLP

[57] ABSTRACT

A bandage has a central portion for application directly to a body wound and a plurality of adhesive tabs connected to and spaced around the central portion for adhesion to the body around and in spaced-apart relation to the wound. Each tab is capable of independent flexion. The bandage can be applied substantially without wrinkling to a wound administered to a convex, concave, or flexing body part, as well as to a wound administered to a body part that is flat and/or immobile. The bandage can be made to adhere reliably, despite any flexing or curvature of the body part.

23 Claims, 3 Drawing Sheets

BANDAGE

BACKGROUND OF THE INVENTION

1. Field of the Invention

This invention relates to an adhesive bandage or wound dressing and more particularly to a first-aid adhesive bandage having a release sheet and specifically designed for securing an absorbent pad to protruding, rounded, contoured and/or flexing as well as flat, immobile areas of the body.

2. Description of the Prior Art

The following patents are of interest:

U.S. Pat. No. 4,832,008 Gilman
4,832,009 Dillon
4,907,579 Kum
5,099,832 Ward
5,244,457 Karami et al
5,275,284 Onotsky
5,333,753 Etheredge First-aid bandages are conventionally applied to superficial cuts, abrasions, punctures, sores, etc., anywhere on the body, usually in conjunction with bacteriological ointment applied to an absorbent gauze pad held in place over the wound by a flexible adhesive backing material.

Over the years since the introduction of the familiar and popular Band Aid, trademark of the Johnson & Johnson Corporation, and Curad, trademark of the Kendall Corporation, improvements have been made in two basic areas: bandage materials and bandage packaging. The development of materials used in the bandages has generally improved the gauze pads' absorbency and ease of release from the wound area and the backing materials' vapor permeability and hydrophobic performance. The development of packaging has led to various designs of that maintain sterility during storage and enable the user to open and apply the bandage without having to touch the adhesive backing or the absorbent gauze pad.

Although first-aid bandages come in a variety of sizes and shapes, their present design limits their effectiveness in covering wounds and staying in place on certain parts of the human anatomy.

There currently exist two major types of bandages: the general-purpose rectangular adhesive strip in three sizes with a centrally located rectangular absorbent gauze pad, and a variety of specially shaped bandages (dots, squares, "H"-shaped and "bow tie"-shaped adhesive bandages) also having centrally located absorbent gauze pads. Although these specially shaped bandages are designed for specific conditions—to cover injection punctures, skin blemishes, etc., or certain areas of the body such as the knee, heel, finger, toe, etc., they usually fail to apply evenly, smoothly or comfortably to convex and concave parts of the body, or to flexing parts of the body. In particular, fingertips, toes, elbows, heels and knees, which are very active points of the body and prone to abrasion and injury, are not well protected by the adhesive bandages known heretofore. Since currently available bandages often do not apply well in these locations, they often do not stay in place well either.

A major flaw in the present assortment of conventional bandages is that, with the exception of the cumbersome "H" and "bow tie" bandages, their flat, planar construction does not enable them to form around a finger or elbow or similar body part without the adhesive backing material wrinkling or bunching up, or in the case of the "bow tie" and familiar rectangular bandages, does not prevent the absorbent gauze area from opening to the elements on the sides or from sliding laterally off the wound.

OBJECTS AND SUMMARY OF THE INVENTION

An object of this invention is to solve the problems of the prior art outlined above. In particular, an object of the invention is to provide a first-aid bandage that will apply evenly, smoothly and comfortably to highly contoured and/or flexing areas of the body, including fingertips, toes, elbows, heels and knees. Another object of the invention is to provide a single bandage design in a variety of sizes that will be equally well suited to flat and simple planar as well as compound curved areas of the body, thus eliminating the need for the consumer to purchase both regular and specialty bandages to apply to different parts of the body.

The bandage of the present invention is designed and cut to provide three self-adhesive tabs plus a centrally located absorbent pad. An adhesive backing is provided consisting of a flexible, breathable, gas-permeable, hydrophobic material. The adhesive backing may be any woven or nonwoven plastic, paper or other suitable material used for bandages now or in the future. The absorbent pad may be any woven or nonwoven cloth or synthetic fiber material used for bandage dressings now or in the future. The shape and cut of the bandage enable it to be applied and fitted securely to any exterior surface of the body. The fit is achieved because the independently flexible self-adhesive tabs, preferably three in number positioned around the central absorbent pad at intervals of 120°, can be wrapped around any convex body contour or bent back to any degree necessary to conform to any concave body contour adjacent to the wound.

The die cuts or slits between the self-adhesive tabs of the backing material do not extend all the way to the outer periphery of the centrally located absorbent material. The reason for this is to provide a continuous adhesive ring completely around the absorbent material in order to seal off the wound from the environment and prevent foreign material from getting into the wound.

The invention provides a bandage that stays in place better than any conventional bandage when applied over wounds on particularly active or highly contoured parts of the body, and that is equally effective for use over wounds in general applications on the body.

BRIEF DESCRIPTION OF THE DRAWINGS

A better understanding of the objects, features and advantages of the invention can be gained from the following detailed description of the preferred embodiments thereof in conjunction with the figures of the appended drawing, wherein like reference characters designate like parts, and wherein.

DESCRIPTION OF THE PREFERRED EMBODIMENTS

Figure 1:
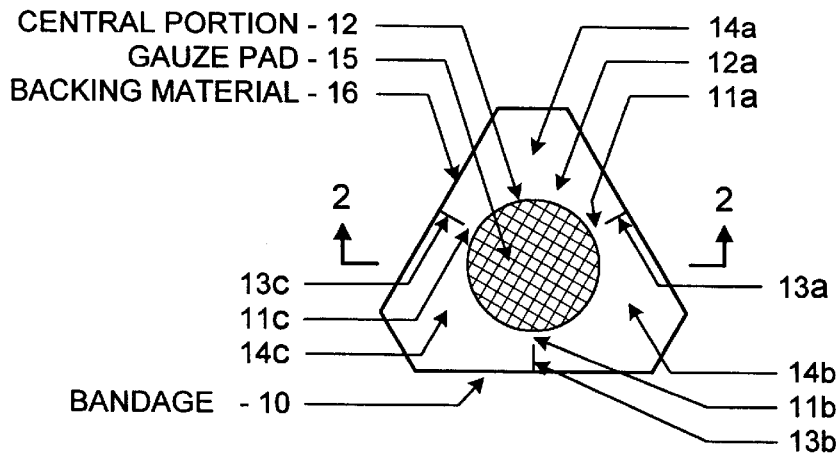
FIG. 1 is a plan view of a preferred embodiment of a bandage constructed in accordance with the present invention, shown without cover sheets.
Figure 2:
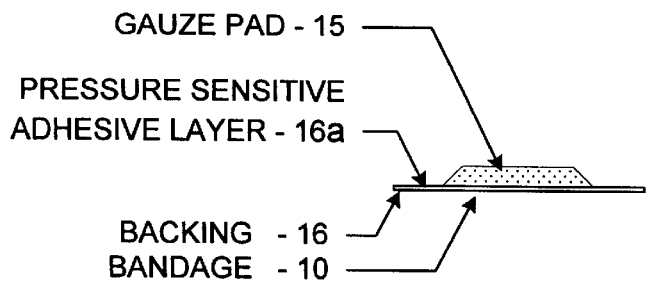
FIG. 2 is in a sectional view of the bandage taken at line AA of FIG. 1.

FIG. 1 shows in plan view a bandage 10 constructed in accordance with the invention. It comprises a central portion 12 for application directly to a body wound (FIG. 7) and a plurality of adhesive tabs 14a, 14b, 14c connected to and spaced around the central portion 12 for adhesion to the body around and in spaced-apart relation to the wound. Each tab 14a, 14b, 14c is capable of independent flexion, whereby the bandage can be applied substantially without wrinkling, folding or puckering (hereinafter without wrinkling) to a wound administered to a convex, concave, or flexing body part (as well as to a plane and/or immobile body part) and made to adhere reliably.

The independent flexion of the three tabs 14a, 14b, 14c is facilitated by three slits 13a, 13b, 13c formed in the bandage 10 respectively between pairs of tabs. The slit 13a separates the tabs 14a and 14c, the slit 13b separates the tabs 14a and 14b, and the slit 13c separates the tabs 14b and 14c. The slits extend to within 1/16" (about 1.6 mm) of the gauze pad 15 and leave spaces 11a, 11b, 11c forming part of an uninterrupted adhesive ring around the gauze pad 15, whereby the gauze pad 15 and the wound it covers can be sealed from the environment.

In the preferred embodiment of the invention, the tabs 14a, 14b, 14c are of identical size and shape and are spaced around the central portion 12 at intervals of 120°. The slits 13a, 13b, 13c are likewise of identical size and shape and spaced around the central portion 12 at intervals of 120°. It is within the scope of the invention, however, to make the tabs different from one another in size and/or shape. It is also within the scope of the invention to make the slits different from one another in size and/or shape. Moreover, the number of tabs and slits can be varied, as those skilled in the art will readily understand.

The bandage backing 16 is formed of a material that is flexible. This material is also preferably breathable, gas-permeable, and hydrophobic. The backing 16 can be made of a material that is woven or nonwoven and opaque, translucent or transparent, and is coated with a pressure-sensitive, hypoallergenic acrylate adhesive layer 16a.

An absorbent pad 15, preferably a gauze pad, is formed on the central portion 12, centered in the backing material 16, and held in place by the adhesive layer 16a. The adhesive bandage surface shown in FIG. 1 is placed on the body surface so that the adhesive layer 16a faces the body and the gauze pad 15 is located over the wound. The three tabs 14a, 14b and 14c are pressed onto the skin adjacent to the wound and automatically assume the form or contour that is most practical and comfortable. In particular, they overlap one another to a progressively greater extent with increasing distance from the central portion 12 if the bandage 10 is applied to a highly contoured surface such as a fingertip.

Figure 3:
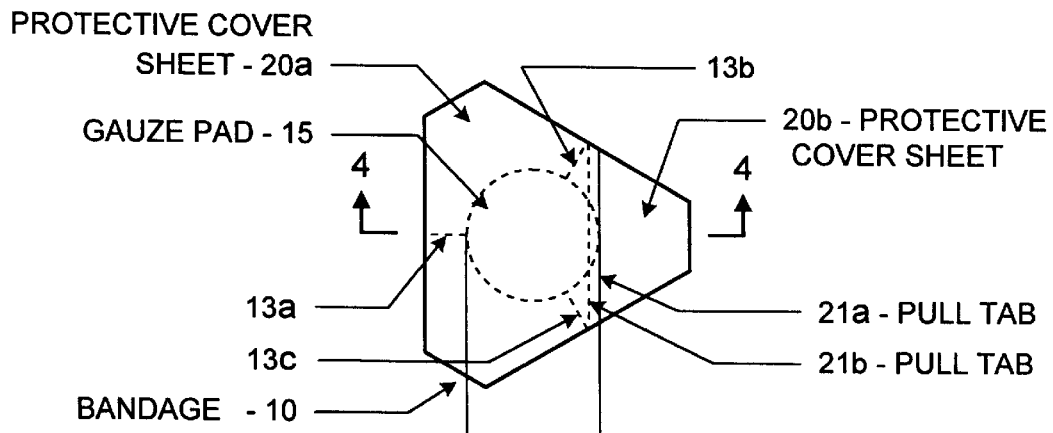
FIG. 3 is a plan view of the bandage showing the configuration of the cover sheets over the bandage's adhesive backing material.
Figure 4:
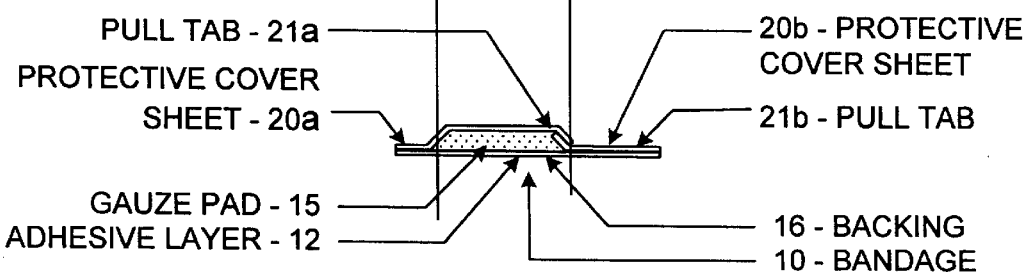
FIG. 4 is a sectional view taken at line BB of FIG. 3.

During manufacture, protective cover sheets 20a and 20b are placed over the adhesive layer 16a, as shown in plan view with the gauze pad 15 ghosted in FIG. 3 and in section in FIG. 4. The cover sheets 20a and 20b keep the gauze pad 15 clean and the adhesive layer 16a covered until application of the bandage 10 is desired. They thus enable the bandage 10 to be handled without deteriorating. The cover sheets 20a and 20b enable a user to manipulate the bandage without touching the gauze pad 15 or adhesive layer 16a of the bandage 10. The protective cover sheets 20a and 20b overlap each other, thus providing pulls 21a and 21b either of which can be grasped between the thumb and index finger and peeled back to expose one or two tabs 14a, 14b, 14c of the backing 16. The remaining cover sheet 20b or 20a provides a finger hold for the bandage so that ointment can be applied to the gauze pad 15 if desired and so that the bandage 10 can be manipulated and positioned over the wound and the user can secure the exposed adhesive tabs 14a, 14b, 14c to the body surface without having to touch the sterile gauze pad 15 or adhesive layer 16a.

Figure 5:
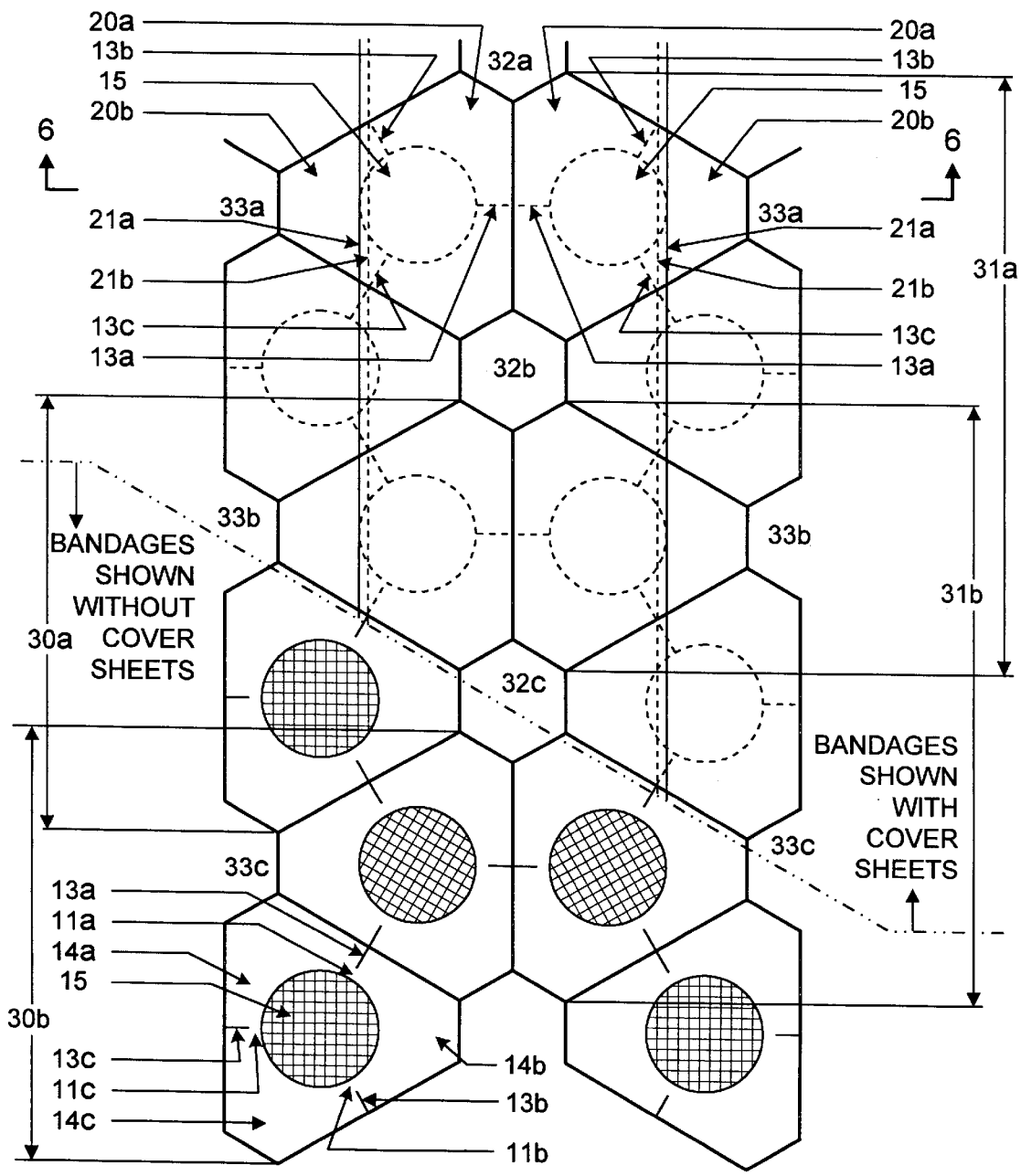
FIG. 5 is a plan view showing the continuous manufacture of a web of multiple bandages according to the present invention, including the continuous application of the cover sheets over the bandages' adhesive backing material and the die cutting pattern by which the web of bandage material is cut into individual bandages.
Figure 6:
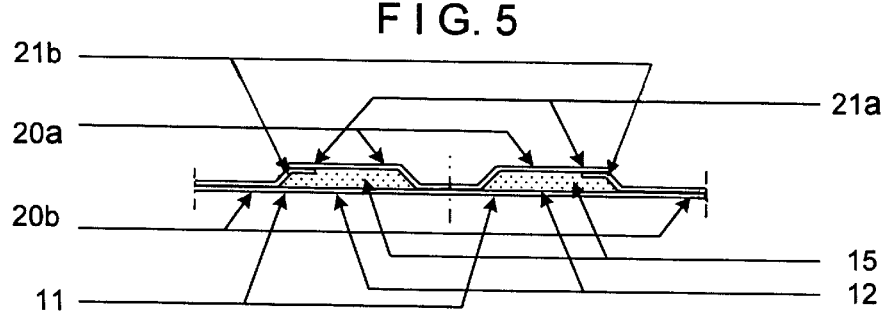
FIG. 6 is a sectional view taken at line CC of FIG. 5.

FIGS. 5 and 6 show one convenient way of manufacturing the bandages. The bandages have generally the shape of equilateral triangles with truncated vertices. From another standpoint they can be viewed as plane geometric shapes having six sides of which three that are relatively long alternate with three that are relatively short, the slits 13a, 13b, 13c being formed in the sides that are relatively long and extending perpendicular thereto. The bandages as manufactured in a web W are nested in groups of four to form a series of U's (or inverted U's) 31a, 31b, etc. From another standpoint they can be viewed as arranged in a plurality of overlapping hexagonal arrays 32a, 32b, etc, adjacent hexagons sharing two bandages. The U's or hexagons nest or overlaps in such a manner as to leave small hexagonal spaces 32a, 32b, etc., in the center of the web W and small trapezoidal indentations 33a, 33b, etc., at the edges.

In FIG. 5 the cover sheets are shown in part applied and, for clarity, in part removed. The bandages are separable from one another along their common sides. This arrangement is very efficient from a manufacturing standpoint, resulting in a minimum of waste product.

Figure 7:
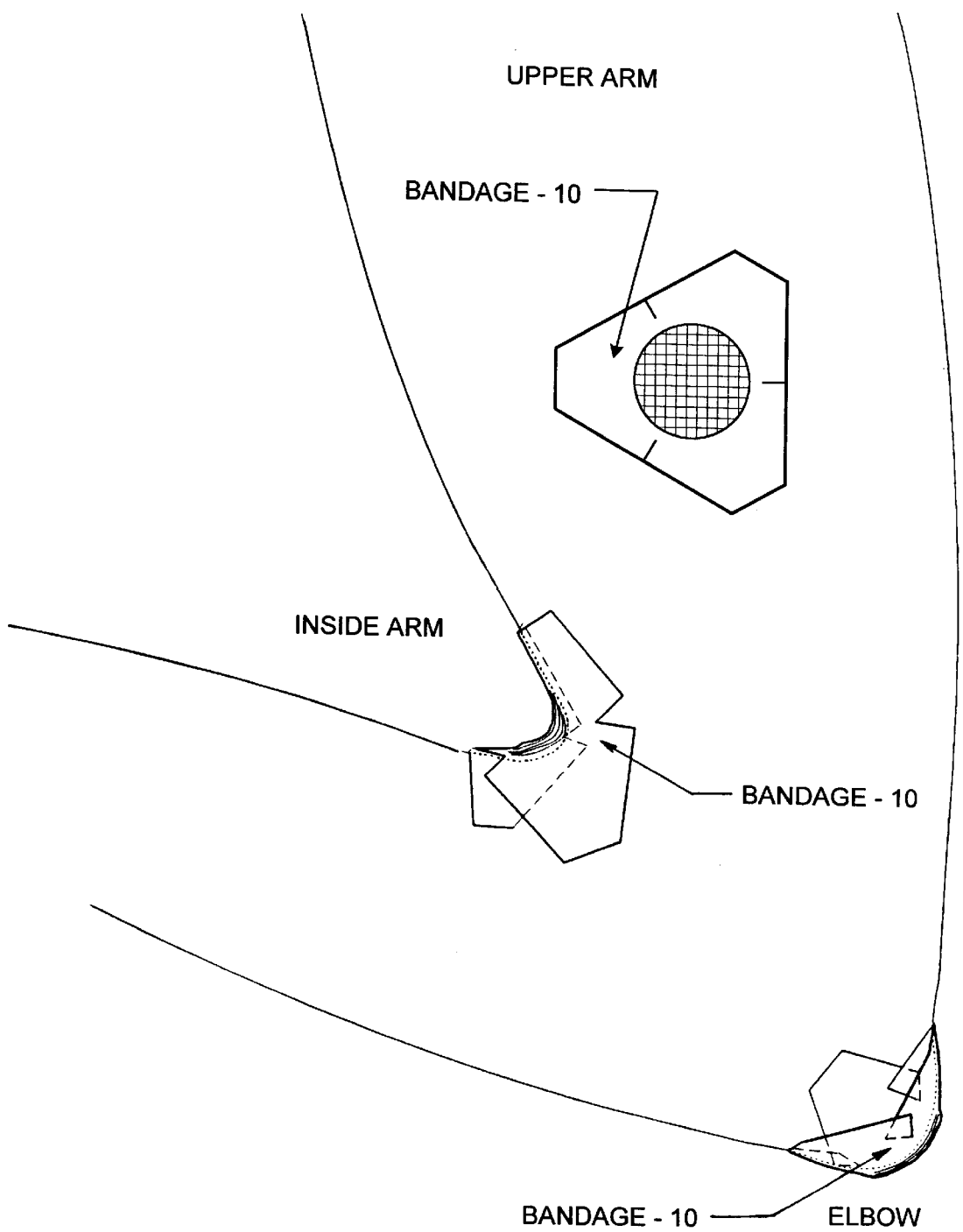
FIG. 7 is a perspective view showing a bandage constructed in accordance with the invention applied to flexing body surfaces that are respectively concave and convex.

In FIG. 7, two bandages 10 are applied respectively to saddle shaped and convex surfaces of an elbow. A saddle shaped surface is one that in convex in a first plane and concave in a second plane normal to the first plane. These surfaces are also flexing, as when the elbow is alternately bent and straightened.

Thus there is provided in accordance with the invention a novel and highly effective bandage that accomplishes the objects of the invention set out above. Many modifications of the preferred embodiments of the invention disclosed above will readily occur to those skilled in the art. The invention therefore extends to all structure and methods that fall within the scope of the appended claims.

I claim:

1. A bandage comprising
   a central portion for application directly to a body wound and
   a plurality of adhesive tabs connected to, spaced around, and extending radially away from the central portion for adhesion to the body around and in spaced-apart relation to the wound, each tab being capable of independent flexion and having a radially outer portion capable of drawing toward or away from a radially outer portion of an adjacent tab, depending on the local body contour adjacent the wound,
   whereby the bandage can be
   applied substantially without wrinkling to a wound in to a contoured or flexing body part and made to adhere reliably.

2. A bandage according to claim 1 wherein the tabs are separated from one another by slits and are substantially contiguous with one another.

3. A bandage according to claim 1 wherein the tabs are separated from one another by slits and are substantially contiguous with one another, further comprising a gauze pad mounted on the central portion and wherein the tabs are adhesive and the slits terminate short of the central portion and leave an uninterrupted adhesive ring around the gauze pad, whereby the gauze pad and a wound covered by it can be sealed from the environment.

4. A bandage according to claim 1 comprising three tabs spaced around the central portion.

5. A bandage according to claim 1 comprising three tabs spaced around the central portion at intervals of 120°.

6. A bandage according to claim 1 further comprising a backing formed of a material that is flexible.

7. A bandage according to claim 1 further comprising a backing formed of a material that is breathable.

8. A bandage according to claim 1 further comprising a backing formed of a material that is gas-permeable.

9. A bandage according to claim 1 further comprising a backing formed of a material that is hydrophobic.

10. A bandage according to claim 1 further comprising a backing formed of a material that is flexible, breathable, gas-permeable and hydrophobic.

11. A bandage according to claim 1 further comprising a backing formed of a material that is woven.

12. A bandage according to claim 1 further comprising a backing formed of a material that is nonwoven.

13. A bandage according to claim 1 further comprising a backing formed of a material that is opaque.

14. A bandage according to claim 1 further comprising a backing formed of a material that is translucent.

15. A bandage according to claim 1 further comprising a backing formed of a material that is transparent.

16. A bandage according to claim 1 further comprising an absorbent pad formed on the central portion.

17. A bandage according to claim 1 further comprising a gauze pad formed on the central portion.

18. A bandage according to claim 1 further comprising a sterile pad formed on the central portion.

19. A bandage according to claim 1 further comprising a sterile gauze pad formed on the central portion.

20. A bandage according to claim 1 further comprising at least one sheet covering the tabs and central portion so that the bandage can be handled without deteriorating.

21. A bandage according to claim 1 further comprising at least one sheet covering the tabs and central portion so that the bandage can be handled without deteriorating, the sheet being formed with a pull facilitating its removal.

22. A bandage according to claim 1 further comprising at least two sheets covering the tabs and central portion so that the bandage can be handled without deteriorating, the sheets overlapping one another in part and each being formed with a pull facilitating its removal.

23. A method of treating a body wound comprising the steps of
   providing a bandage having a central portion for application directly to the wound,
   forming a plurality of independently flexible adhesive tabs connected to, spaced around, and extending radially away from the central portion,
   applying the central portion directly to the wound,
   moving radially outer portions of adjacent tabs toward or away from each other depending on the local body contour adjacent the wound, and
   adhering the tabs to the body around and in spaced-apart relation to the wound.

* * * * *